(12) United States Patent
Chiba

(10) Patent No.: US 8,865,475 B2
(45) Date of Patent: Oct. 21, 2014

(54) METHOD OF REACTING TWO-PHASE SOLUTION CHANGING IN PHASE STATE WITH TEMPERATURE CHANGE AND APPARATUS FOR PRACTICING THE SAME

(75) Inventor: Kazuhiro Chiba, Musashino (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 277 days.

(21) Appl. No.: 13/233,279

(22) Filed: Sep. 15, 2011

(65) Prior Publication Data

US 2012/0032110 A1 Feb. 9, 2012

Related U.S. Application Data

(62) Division of application No. 10/574,851, filed as application No. PCT/JP2004/015096 on Oct. 6, 2004, now abandoned.

(30) Foreign Application Priority Data

Oct. 8, 2003 (JP) .................................. 2003-349016
Nov. 4, 2003 (JP) .................................. 2003-374234

(51) Int. Cl.
*G01N 1/18* (2006.01)
*C07B 61/00* (2006.01)

(52) U.S. Cl.
CPC ........ *C07B 61/00* (2013.01); *B01J 2219/00599* (2013.01); *B01J 2219/00308* (2013.01); *B01J 2219/00481* (2013.01); *B01J 2219/00585* (2013.01); *B01J 2219/0072* (2013.01); *B01J 2219/00686* (2013.01); *B01J 2219/00495* (2013.01); *B01J 2219/00364* (2013.01)
USPC ................................. 436/178; 436/177; 436/4

(58) Field of Classification Search
CPC ................................................... B01D 2256/24
USPC ............................... 436/4, 177, 178; 530/338
See application file for complete search history.

(56) References Cited

U.S. PATENT DOCUMENTS

| 3,480,516 | A | * | 11/1969 | Tindall ............................ 203/66 |
| 5,382,745 | A | * | 1/1995 | Spohn et al. ................... 585/800 |
| 2001/0036898 | A1 | | 11/2001 | Horhota et al. |
| 2003/0148481 | A1 | | 8/2003 | Theil et al. |
| 2003/0157721 | A1 | | 8/2003 | Turner et al. |

FOREIGN PATENT DOCUMENTS

| EP | 0 882 500 A1 | 12/1998 |
| JP | 64-61497 | 3/1989 |
| JP | 2000-218155 | 8/2000 |
| JP | 2003-62448 | 3/2003 |
| JP | 2004-35521 | 2/2004 |

OTHER PUBLICATIONS

Horvath, István et al., "Facile Catalyst Separation Without Water: Fluorous Biphase Hydroformylation of Olefins", Science, vol. 266, pp. 72-75, 1994.
Gladysz, J. A., "Are Teflon "Ponytails" the Coming Fashion for Catalysts?", Science, vol. 266, pp. 55-56, 1994.
Kazuhiro Chiba, et al.,"A Liquid-Phase Peptide Synthesis in Cyclohexane-Based Biphasic Thermomorphic Systems", Royal Society of Chemistry, XP008076759, 2002, 3 pages.

* cited by examiner

*Primary Examiner* — Natalia Levkovich
(74) *Attorney, Agent, or Firm* — Oblon, Spivak, McClelland, Maier & Neustadt, L.L.P.

(57) ABSTRACT

A method for making a number (N) of samples react under the same reaction conditions that includes heating a number of reaction containers simultaneously and maintaining the reaction containers at a predetermined temperature; placing a sample in each heated reaction chamber and maintaining a two-phase solution at a predetermined temperature; stirring the sample that is heated to the predetermined temperature to create a uniform solution, which is maintained for a predetermined time; and cooling the uniform solution without cooling the reaction container after the predetermined period of time has passed so as to gain a two-phase solution within the reaction container, where the samples have a solution where the phase state of a reaction solvent changes in a reversible manner between a two-phase solution state and a uniform solution state when the temperature fluctuates over or under a certain constant temperature.

16 Claims, 4 Drawing Sheets

METHOD OF REACTING TWO-PHASE SOLUTION CHANGING IN PHASE STATE WITH TEMPERATURE CHANGE AND APPARATUS FOR PRACTICING THE SAME

TECHNICAL FIELD

The present invention relates to a method for making a two-phase solution of which the phase state changes as a result of temperature conversion react, of which the operability and reproducibility are excellent, as well as to an apparatus for implementing this.

BACKGROUND TECHNOLOGY

In a chemical process, in the case where a sequential mixture and separation operation can be carried out with ease, sequential work efficiency can be dramatically increased. Presently, it is known that change in temperature causes phase solving/phase separation in a solvent mixture that is formed of a combination of a solvent having a perfluoroalkyl group, and a general organic solvent (I. T. Horvath, J. Rabai, Science, 1994, 266, 72; J. A. Gladysz, Science, 1994, 266, 55).

Japanese Unexamined Patent Publication H15 (2003)-62448 shows a combination of a cycloalkane and a polar solvent as an example of a solvent mixture where phase solving/phase separation is caused. Such solution phase solving and separation phenomena, where phase solving and phase separation can be made to repeat by slightly changing the temperature, can be applied to a wide range of chemical processes, from the micro and macro scale to the plant level. Recently, a method for making a number of processes progress simultaneously, where combinatorial chemistry or a high throughput process method is carried out in a tabletop apparatus, is used widely in many test and research institutions.

FIG. 4 is a conceptual diagram illustrating the theory that solvent mixture causes phase solving/phase separation. (A) in FIG. 4 shows a state where single organic solvents or mixed organic solvents are separated. For example, a solvent that dissolves a reactive material is used as one solvent, and a solvent that dissolves a catalyst or a reaction adjuvant is used as the other solvent. (B) is a step where reaction progresses under such temperature conditions that the solvent is in a state where a uniform phase solving mixture solvent system. (C) shows the state of a separated solvent system where solvent phases of which the main components are solvents that form reversible solvent systems under the above described temperature conditions are separated into phases in which products are dissolved and catalysts or a reaction adjuvant are dissolved. Then, the phase in which the products are dissolved (product solution) is separated and taken out so as to be used for a desired application, while the phase in which reaction adjuvant dissolves (catalyst or reaction adjuvant solution) is recycled (D).

One example of an automatic synthesizing method which uses the theory that such a solvent system causes phase solving/phase separation is described in reference to FIG. 3. That is to say, a material such as a reagent is injected into a reaction container 11 using a sampling apparatus 12 so that a two-phase solution (I) is gained. Next, reaction container 11 is heated, so that the two-phase solution becomes a uniform solution where reaction starts (II). After reaction has started and a predetermined period of time has passed, cooling is started (III). The solution in reaction container 11 automatically separates into phases when the temperature has been lowered to a predetermined temperature or lower (IV). Next, the product phase in reaction container 11 is extracted using an extraction apparatus 17 (V), and this product solution 16 is used for animal experimentation, which is an activity assay, or used for analysis (VI). According to a method for making a number of processes progress simultaneously, several tens to one hundred or more reaction systems, one of which is, for example, that shown in FIG. 3, are carried out in the same apparatus and under the same reaction conditions.

However, it is structurally very troublesome to individually control the temperature of several tens to one hundred or more containers in a tabletop apparatus. Therefore, an apparatus where a block heater which can heat all of the several tens to one hundred or more containers simultaneously is built in is conventionally used. In this case, an automatic sampling operation is carried out on each sample sequentially and automatically, and after that, all the containers are simultaneously heated. In addition, after the solution has been converted into a uniform solution and reaction is complete, all the containers are cooled simultaneously. According to this method, the period of time that is required from the start of the automatic sampling operation to the start of the heating differs, depending on the container. After the automatic sampling, though the solution is in a two-phase state before the start of the reaction, in which, theoretically, no reaction occurs, in reality, a slight amount of reaction occurs even in the two-phase state, since there is contact between the phases in the interface portion. As described above, all of the process conditions are different, depending on the container, according to the conventional method, and it is impossible to carry out the process under the same conditions. This has caused many problems with reproducibility in chemical processes.

Meanwhile, in the case where a multi-stage successive reaction process is carried out by repeating successive phase solving/phase separation, the temperature of the reaction containers should be increased or lowered at each stage, and thereby, the temperature of the solution changes, so that the phase structure of the solution changes. This causes a problem, such that control becomes difficult, particularly on a plant scale, where the capacity is large. In addition, when the temperature of the reaction containers on a plant scale is increased or lowered at each stage, a problem arises, such that the amount of use of utilities, such as electrical power and cooling water, becomes massive, increasing the cost for manufacture.

Accordingly, an object of the present invention is to provide a method for making a two-phase solution of which the phase state changes as a result of temperature conversion react in a number of processes, where a chemical process can be carried out on a number of samples under the same conditions in one processing apparatus, and which is excellent in operativity and reproducibility, as well as an apparatus for implementing this. In addition, another object of the present invention is to provide a method for making a two-phase solution of which the phase state changes due to temperature conversion which is excellent in operativity and efficiency in production, as well as an apparatus for implementing this.

(Non-Patent Document 1) I. T. Horvath, J. Rabai, Science, 1994, 266, 72; J. A. Gladysz, Science, 1994, 266, 55

(Patent Document 1) Japanese Unexamined Patent Publication H15 (2003)-62448 (Claim 1)

DISCLOSURE OF THE INVENTION

Under these circumstances, the present inventors conducted diligent research, and as a result, discovered that phase separation automatically occurs when the temperature is lowered, while phase solving does not occur even when the temperature is increased, unless provided with certain physical stimulation, in a solvent mixture where phase solving and phase separation are repeated in a reversible manner, by changing the temperature; accordingly, the two-phase solution is maintained even when the uniform solution within the container is cooled without cooling the container that has been heated in order to make reaction occur, so that the two-phase solution is gained, and after that, the two-phase solution is kept within the container in this heated condition; accordingly, a multi-stage successive reaction process can be carried out while maintaining the temperature of the reaction container, even after the product solution has been removed from the two-phase solution, and as a result, excellent operativity and efficiency in production can be gained; furthermore, according to a method for making a number of processes progress simultaneously using these solvent properties, the respective samples can all be placed under the same conditions in the case where the respective steps of automatic sampling, stirring, inducing reaction and separating are carried out for the same period of time for all of the samples, even when there is a difference between the starting times of the operations that are carried out on the respective samples after a number of reaction containers have been simultaneously heated, so that excellent operativity and reproducibility can be achieved, and thus, the present invention was completed.

That is to say, a first invention provides a method for carrying out a number of processes in a two-phase solution of which the phase state changes as a result of temperature conversion, which is a method for making a number of samples react under the same reaction conditions, wherein these samples are dissolved in a reaction solvent, where the phase state of the solution changes in a reversible manner between a two-phase solution state and a uniform solution state when the temperature fluctuates over or under a certain constant temperature, and processes are carried out sequentially in the respective steps: (A) the constant container heating step, where a number of reaction containers are simultaneously heated, and these reaction containers are maintained at a predetermined temperature; (B) the sample heating step, where samples are automatically put into the heated reaction containers, and the two-phase solution has a predetermined temperature; (C) the reaction step, where the samples that have been heated to the predetermined temperature are stirred, so that uniform solutions are gained, which are maintained in the same state for a predetermined period of time; and (D) the cooling step, where after a predetermined period of time has passed, the uniform solutions are cooled without cooling the reaction containers, so that two-phase solutions are gained within the reaction containers, and wherein the method is characterized in that the successive operation is carried out in such a manner that the period of time ($t_B$) from the start of sampling to the start of stirring, and the period of time ($t_C$) from the start of stirring to the start of cooling become the same for all of the samples.

In addition, the present invention provides an apparatus for inducing a number of reaction processes in a two-phase solution where the phase state changes as a result of temperature conversion, having: a heating means for simultaneously heating a number of reaction containers and maintaining the temperature of the reaction containers at a predetermined temperature; an automatic sampling means for putting samples into the reaction containers; a stirring means for stirring the samples within the reaction containers; a cooling means for cooling uniform solutions within the reaction containers without cooling the reaction containers so that two-phase solutions are gained within the reaction containers; and a control means for controlling the time of the start of operation and the time of the stop of the operation in the respective operations: the sampling operation using the sampling means, the stirring operation using the stirring means, and the cooling operation using the cooling means.

In addition, a second invention provides a method for making a two-phase solution of which the phase state changes as a result of temperature conversion react, characterized by having: a reaction step, where a material solution of which the reaction solvent is a solution of which the phase state changes in a reversible manner between a two-phase solution state and a uniform solution state when the temperature fluctuates over or under a certain constant temperature is stirred at a predetermined temperature within a reaction container, so that a uniform solution is gained and reaction occurs; and a cooling step, where the uniform solution is cooled without cooling the reaction container, so that a two-phase solution is gained within the reaction container.

In addition, the present invention provides an apparatus for making a two-phase solution of which the phase state changes as a result of temperature conversion react, characterized by having: a heating means for heating a reaction container; a reaction container with a stimulation means for providing physical stimulation to a material solution within the reaction container so that a uniform solution is gained attached thereto; and a cooling means for cooling a uniform solution within the reaction container without cooling the reaction container.

According to the first invention, a chemical process can be carried out on a number of samples under the same conditions in one processing apparatus. The configuration of the apparatus and the work process become simple, and the apparatus can operate automatically, making it excellent in productivity and reproducibility. In addition, according to the method for making a two-phase solution of which the phase state changes as a result of temperature conversion react of the second invention, cooling and reheating of one reaction container become unnecessary, and the temperature can be maintained constant, and therefore, efficiency in production greatly increases. In addition, after the completion of reaction in one process, the temperature of the reaction solution where the next reaction is to occur in the process becomes quickly constant (heated condition), and therefore, the period of time for the changing of the temperature can be greatly shortened in a multi-stage successive process or the like.

BEST MODE FOR CARRYING OUT THE INVENTION

First, the first invention is described.

The present invention provides a method which relates to a method for making a number of processes progress simultaneously, according to which a number, for example, several tens or one hundred and several tens, of samples are made to react under the same reaction conditions. As for this method for making a number of processes progress simultaneously, combinatorial chemistry and a method for carrying out a high throughput process in a tabletop apparatus can be cited as examples.

A solution of which the phase state changes in a reversible manner between a two-phase solution state and a uniform solution state when the temperature fluctuates over and under a certain constant temperature (hereinafter referred to as "solvent mixture") is used as a reaction solvent for the samples. This solvent mixture is not particularly limited, and, for example, a solvent mixture of an organic solvent having a low polarity and an organic solvent having a high polarity can be cited. As the organic solvent having a low polarity, alkane, cycloalkane, alkene, alkyne and aromatic compounds can be cited as examples. From among these, cycloalkane compounds are preferable, and in particular, cyclohexane is preferable, as its melting point is 6.5° C., which is relatively high, and the product after the reaction can be solidified and separated.

As the organic solvent having a high polarity, nitroalkane, nitrile, alcohol, alkyl halide, ether, urea, amide compounds and sulfoxide can be cited as examples, and one type from among these can be used alone, or two or more types can be combined for use. The above described samples include substances which relate to a variety of reactions, such as solutes, solvents, stromata and reaction adjuvants, in addition to solvent mixtures as those described above.

Figure 1:
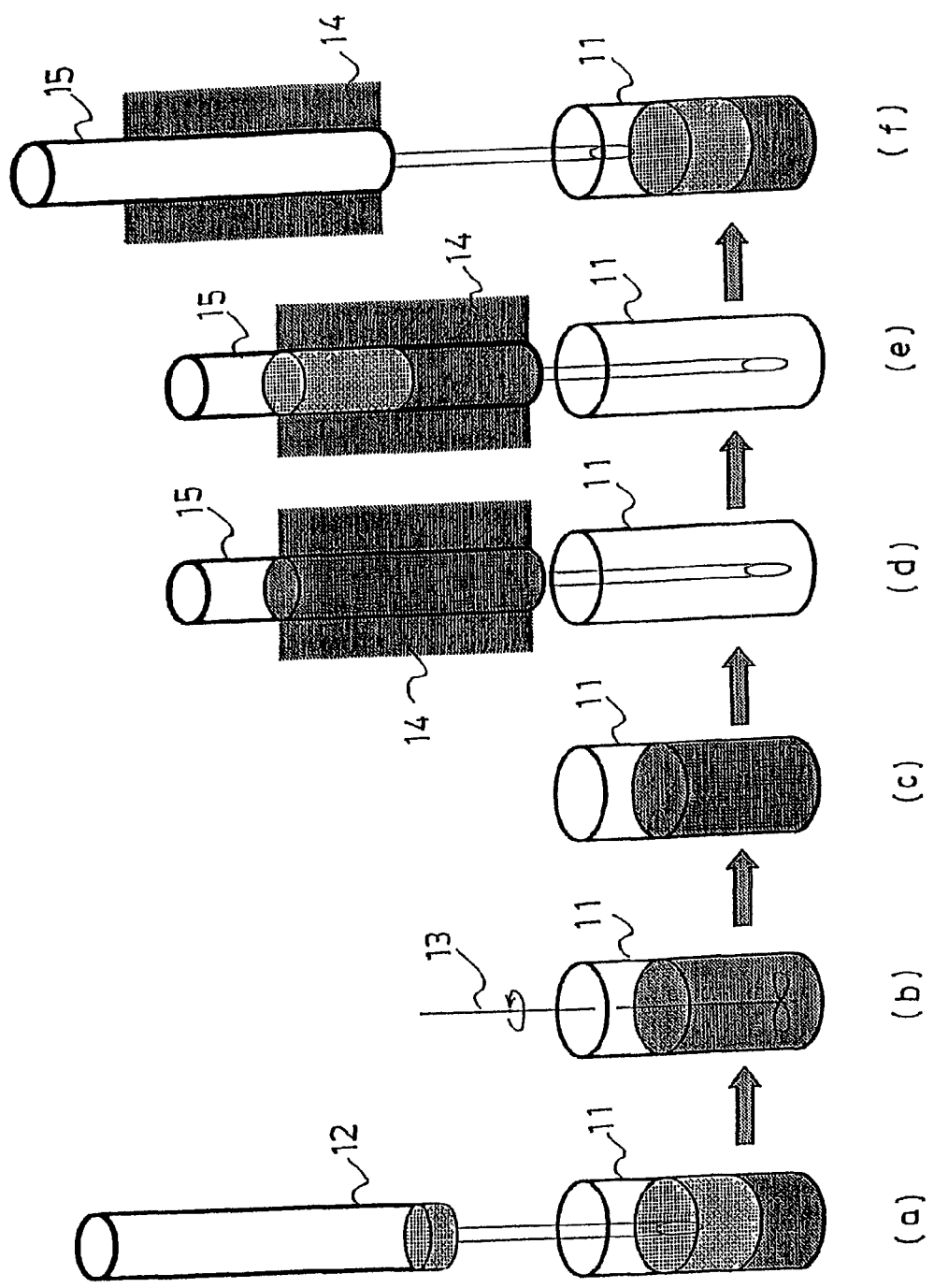
FIG. 1 is a diagram illustrating the respective reaction steps in one sample in accordance with a method for causing reaction in a number of processes according to a first invention.

Next, the reaction method of the present invention is described in reference to FIG. 1. FIG. 1 illustrates the respective reaction steps in one sample, and the apparatus portions and a great number of other reaction containers are omitted. Reaction containers 11 have the same form for all of the samples, and the sample amount, the heating conditions and the cooling conditions are the same. As shown in FIG. 1, the respective samples are processed sequentially in the respective steps: (A) the constant container heating step, where a number (N) of reaction containers 11 are simultaneously heated, and these reaction containers 11 are maintained at a predetermined temperature (not shown); (B) the sample heating step, where samples are automatically put into the heated reaction containers, and the two-phase solution has a predetermined temperature ((a) in FIG. 1); (C) the reaction step, where the samples that have been heated to the predetermined temperature are stirred, so that uniform solutions are gained, which are maintained in the same state for a predetermined period of time ((b) and (c) in FIG. 1); and (D) the cooling step, where, after the completion of the reaction step, the uniform solutions are cooled without cooling the reaction containers, so that two-phase solutions are gained within the reaction containers ((d) to (f) in FIG. 1).

The constant container heating step of (A) is a step where reaction containers, which have been installed in a number (N) of container containing portions, are maintained at a predetermined temperature ($t_0$) in a tabletop apparatus into which a block heater is built, and which is provided with the container containing portions where a part or the entirety of a reaction container can be placed in each of the container containing portions. Though the predetermined temperature ($t_0$) is not particularly limited and may be any temperature between room temperature and the reaction temperature, in the case where this is set to the reaction temperature, this temperature may simply be maintained throughout all of the reaction steps afterwards, and the temperature setting and the temperature control operation become easy. After step (A), all N reaction containers are maintained at the predetermined temperature ($t_0$).

The sample heating step of (B) is a step where samples are put into the heating reaction containers, which are heated to a predetermined temperature ($t_1$), where the two-phase solution is maintained. As for the method for putting samples into the heating reaction containers, a method for sampling using a known sampling apparatus 12 can be used. The predetermined temperature ($t_1$) is the reaction temperature of the two-phase solution. Accordingly, in the case where the predetermined temperature ($t_0$) in step (A) is the reaction temperature, the predetermined temperature ($t_0$) and the predetermined temperature ($t_1$) are the same temperature.

In step (C), the method for stirring the samples that have been heated to the predetermined temperature ($t_1$) is not particularly limited, and a mechanical stirring method for stirring with a stirring rod with stirring blades at the end portion, a bubbling method for introducing bubbles by making a nitrogen gas be blown into the samples and a vibration stirring method for providing vibrations to the sample containers or the samples can be cited as examples. From among these, a mechanical stirring method for stirring with a stirring rod 13, as shown in (b) in FIG. 1, is preferable because a simple apparatus is used and the stirring efficiency is high. The solvent mixture that is used in the present invention is not converted to a uniform solution simply by being heated to the predetermined temperature ($t_1$), and phase solving occurs by providing a certain physical stimulation. Accordingly, the stirring conditions in step (C) are appropriately selected as the conditions in which a uniform solution can be gained. In addition, the predetermined period of time for keeping the solution uniform is the period of, time for reaction and is appropriately determined depending on the used solvents, the type of reaction and the purpose of the reaction. In the solvent mixture that is used in the present invention, phase separation automatically occurs when the temperature is lowered, and therefore, this uniform solution is maintained at a temperature that is no lower than the temperature where such phase separation occurs during the above described predetermined period of time.

In the cooling step of (D), though the method for cooling the uniform solution without cooling the reaction container is not particularly limited, a method for absorbing the uniform solution within the reaction container by means of a syringe with a cooling apparatus so that the uniform solution is cooled within this syringe, a method for placing a solid of which the temperature is lower than that of the reaction container into the uniform solution within the reaction container and a method for mixing a low boiling point compound directly into the uniform solution within the reaction container can be cited. "Without cooling the reaction container" means to exclude cooling the sample within the reaction container by cooling the reaction container, and to include cooling of the reaction container that accompanies cooling the sample within the reaction container.

As for the method for cooling within the above described syringe, as shown in (d) in FIG. 1, a method for absorbing the uniform solution within reaction container 11 by means of a syringe 15 with a cooling apparatus 14 can be cited. As for cooling apparatus 14, an apparatus for making water flow through a jacket (not shown) formed around the cylinder of syringe 15, for example, can be used. In addition, as for the low boiling point compound that is mixed with the uniform solution within the reaction container, n-heptane, having a boiling point of 25° C., can be cited as an example. When a low boiling point compound makes direct contact with the uniform solution within the reaction container, it absorbs evaporation heat from the solution, thus cooling the solution. The uniform solution that is cooled in accordance with the above described method automatically separates into two phases when the temperature becomes a predetermined temperature or lower ((e) in FIG. 1).

In the cooling step of (D), a two-phase solution is gained within the reaction container after cooling. In the case where the cooling method is a method where a solid having a low temperature is used or a method where a low boiling point compound is used, phase separation occurs within the reaction container, and therefore, the system is left as it is without adopting a specific operation. Meanwhile, in the case of a method for cooling within a syringe, the two-phase solution that has been gained within syringe 15 is put back into this reaction container 11. As for the cooling method in the cooling step of (D), a method for absorbing the uniform solution within the reaction container by means of a syringe with a cooling apparatus so that the solution is cooled within the syringe is preferable. That is to say, in the case of cooling within the reaction container by using a solid having a low temperature or a low boiling point compound, the reaction container in a heated state is also cooled, and the cooling efficiency becomes poor. Furthermore, since the reaction container is cooled, it becomes necessary to heat the reaction container again when the remaining solvent is used again after the product solution has been extracted, and thus, the cost for reaction increases. In contrast, in the method for cooling within a syringe, only the reaction solution is cooled, and thus, the cooling efficiency is high. In addition, no physical stimulation is provided to the two-phase separated solution which is put back into the reaction container in a heated state, even if the two-phase separated solution has been heated, and therefore, the state where the two phases are separated can be maintained. Therefore, it becomes unnecessary to heat the reaction container again when the remaining solvent is used again after the product solution has been extracted, and thus, the cost for reduction can be reduced. In an apparatus which has a great number, one hundred and several tens, of the reaction containers, the amount of energy saved from being consumed becomes great when the temperature of the reaction containers is maintained as it is without cooling before using them again.

According to the present invention, successive operations are carried out in such a manner that the period of time ($t_B$) from the start of sampling to the start of stirring, and the period of time ($t_C$) from the start of stirring to the start of cooling become the same for all of the samples. These successive operations are not particularly limited, and a method for successive operations for each step where the above described step (B) is carried out on one to N sample(s), next, the above described step (C) is carried out on one to N sample(s) and finally, the above described step (D) is carried out on one to N sample(s), and a method for successive operations for each sample where the above described steps (B) to (D) are carried out on one sample from among a number (N) of samples, next, the above described steps (B) to (D) are carried out on the second sample with this procedure being sequentially repeated, and finally, the above described steps (B) to (D) are carried out on the N'th sample can be cited as examples. In addition, a number (N) of samples may be divided into groups so that the above described successive operations can be carried out on each divided group. In the case where successive operations are carried out on each divided group, the required periods of time $t_B$ and $t_C$ are made to be the same for all the samples.

Figure 2:
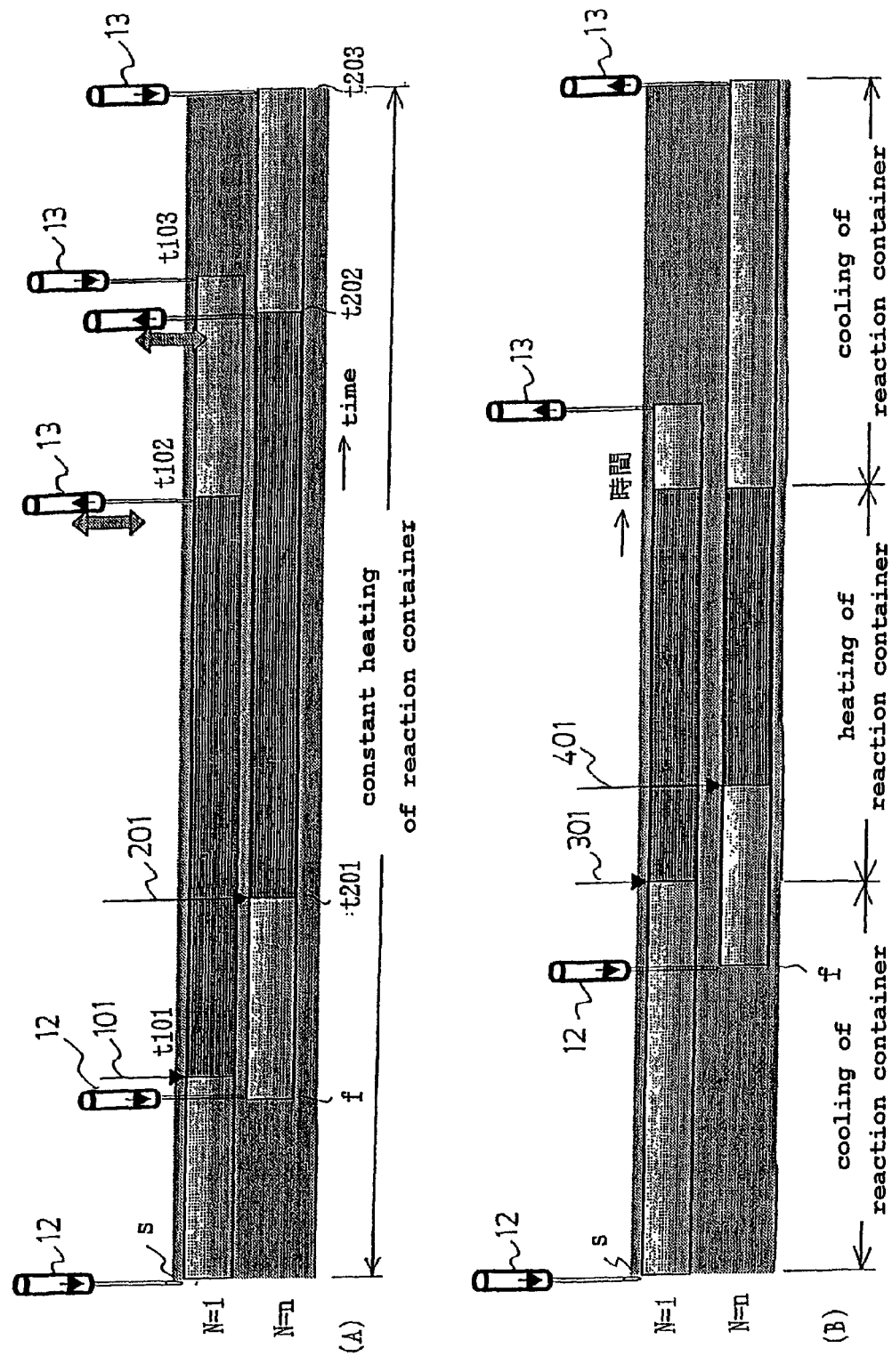
FIG. 2(A) is a diagram showing the relationship between the time that has passed between the first sample (N=1) and the last sample (N=n), and the response steps in accordance with a method for causing reaction in a number of processes according to the first invention.
FIG. 2(B) is a diagram showing the relationship between the time that has passed between the first sample (N=1) and the last sample (N=n), and the response steps in accordance with the prior art.
Figure 3:
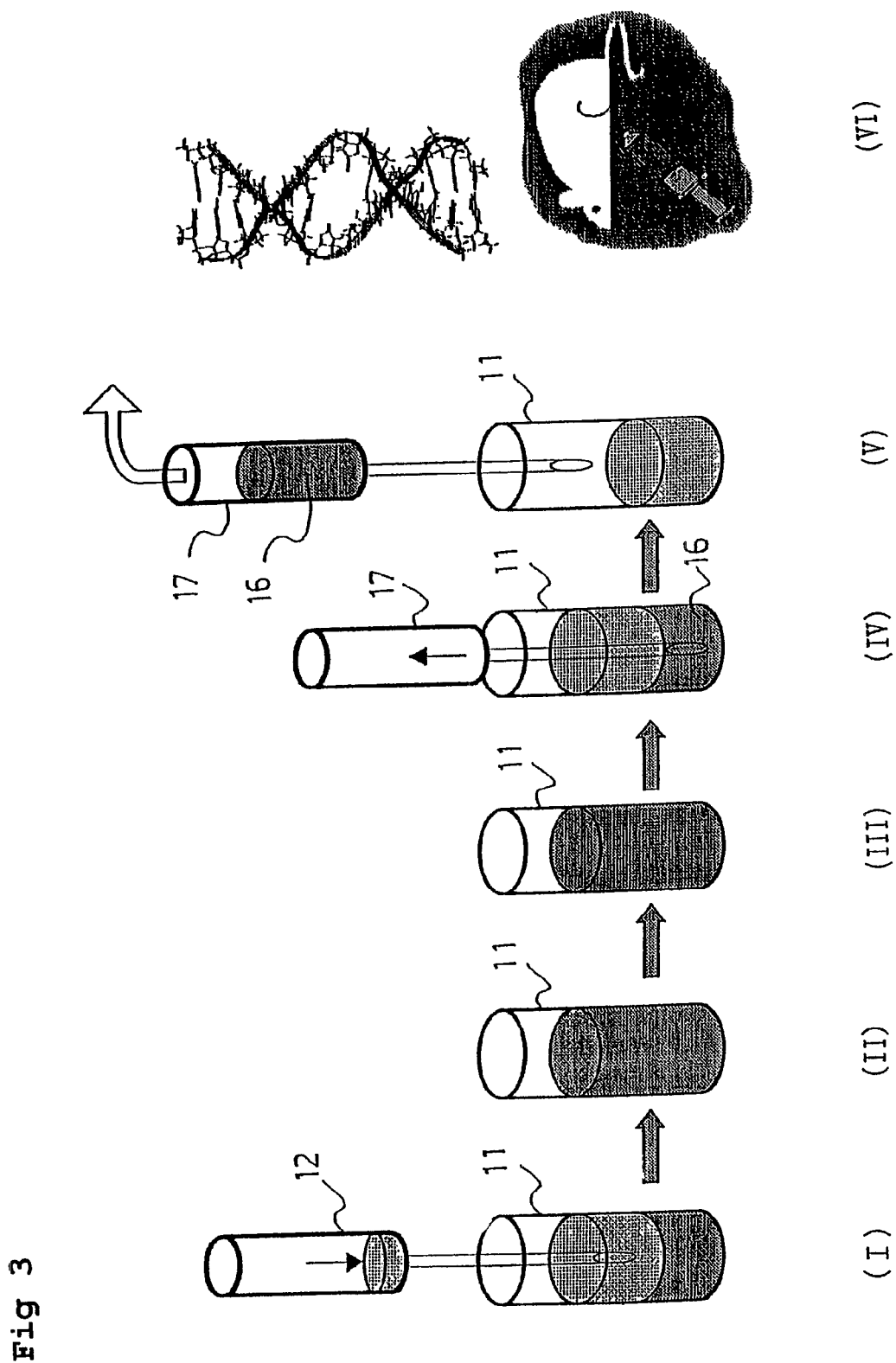
FIG. 3 is a diagram illustrating the respective reaction steps in one sample in accordance with a method for causing reaction in a number of processes according to the prior art.
Figure 4:
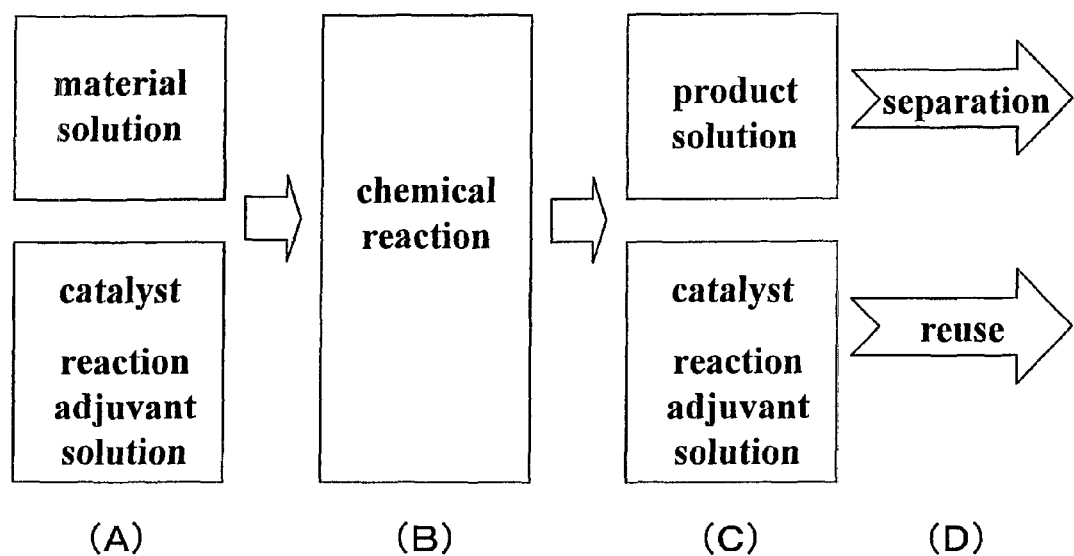
FIG. 4 is a schematic diagram illustrating the thesis that a solvent mixture causes phase solving/phase separation.

Next, a method for successive operations for each step is described in reference to FIG. 2(A). FIG. 2(A) shows the relationship between the time that has passed between the first sample (N=1) and the final sample (N=n), and the reaction steps. In addition, FIG. 2(B) shows the relationship between the time that has passed between the first sample (N=1) and the final sample (N=n), and the reaction steps according to a conventional method. Here, in FIG. 2, the reaction containers are omitted and a change in the sample state within the reaction containers is indicated by the gradation of the shading within oblong quadrilaterals.

In FIG. 2(A), a number of reaction containers are in a state of being heated to a constant reaction temperature in the constant container heating step. First, a sampling apparatus 12 is used to put the first sample (N=1) into the first reaction container (symbol s in FIG. 2). The same operation is carried out sequentially on each sample, and after that, sampling apparatus 12 is used to put the last sample (N=n) into the last reaction container (symbol f in FIG. 2). Next, after the sampling, the first sample that has reached the reaction temperature after time $t_{101}$ has passed is stirred (arrow 101) so that a uniform solution is gained, and this is left undisturbed, leading to the reaction step. After the same operation has been carried out sequentially on each sample, the last sample that has reached the reaction temperature after the sampling and time $t_{201}$ has passed is stirred (arrow 201) so that a uniform solution is gained, and this is left undisturbed, leading to the reaction step. Next, the first sample after time $t_{102}$ has passed is absorbed by a syringe 13 with a cooling apparatus so as to be cooled within syringe 13. Next, cooling is completed in time $t_{103}$, and the solution that has been separated Into two phases is put back into the original reaction container. After the same operation has been carried out sequentially on each sample, the last sample is absorbed by a syringe 13 with a cooling apparatus after time $t_{202}$ has passed so as to be cooled within syringe 13. Next, cooling is completed in time $t_{203}$, and the solution that has been separated into two phases is put back into the original reaction container. The operations shown in FIG. 2(A) are carried out in such a manner that the period of time from the start of sampling to the start of stirring, the period of time from the start of stirring to the start of cooling and the period of time for cooling become the same for all samples. That is to say, s to $t_{101}= \ldots =$f to $t_{201}$, $t_{101}$ to $t_{102}= \ldots =t_{201}$ to $t_{202}$, and $t_{102}$ to $t_{103}= \ldots =t_{202}$ to $t_{203}$. According to the method of FIG. 2(A), the two-phase separated solution that includes the reaction product solution, which is the final product, can be gained within the original heated reaction container, and therefore, a chemical process can be carried out on a number of samples under the same conditions in one process apparatus.

Meanwhile, in FIG. 2(B), showing a conventional method, the reaction container is being cooled. First, a sampling apparatus 12 is used to put the first sample (N=1) into a reaction container (symbol s in FIG. 2(B)), and the same operations are carried out sequentially on each sample, and after that, the final sample (N=n) is put into a reaction container (symbol f in FIG. 2(B)) so that the sampling operation on all samples is completed, and then, the reaction containers are simultaneously heated. Then, the first sample is stirred (arrow 301), and the same operation is carried out sequentially on each sample, and after that, the last sample is stirred (arrow 401), and then, after a predetermined period of time has passed, all of the reaction containers are cooled simultaneously so that a solution that is separated into two phases is gained in each reaction container. In accordance with this method, the process conditions all differ for each container and a chemical process cannot be carried out under the same reaction conditions.

In addition, an apparatus for inducing a number of reaction processes in a two-phase solution where the phase state changes as a result of temperature conversion according to the present invention is provided with: a heating means for simultaneously heating a number of reaction containers and maintaining the temperature of the reaction containers at a predetermined temperature; an automatic sampling means for putting samples into the reaction containers; a stirring means for stirring the samples within the reaction containers; a cooling means for cooling uniform solutions within the reaction containers without cooling the reaction containers, so that two-phase solutions are gained within the reaction containers; and a control means for controlling the time of the start of operation and the time of the stop of the operation in the respective operations: the sampling operation using the sampling means, the stirring operation using the stirring means, and the cooling operation using the cooling means.

The heating means for simultaneously heating a number of reaction containers and maintaining the temperature of the reaction containers at a predetermined temperature has, for example, a block heater built into the heating means, and is provided with a number (N) of container containing portions where apart or the entirety of a reaction container can be placed into each of the container containing portions, and as for this, a tabletop apparatus with a temperature control mechanism for controlling the temperature of the reaction containers can be used.

As for the stirring means for stirring a sample within a reaction container, a stirring rod which is provided with stirring blades at an end portion, a bubbling apparatus that is provided with a bubble introducing tube for introducing bubbles into a sample, and a bubble generator and a vibrator for providing vibration to a sample container or a sample can be cited as examples.

As for the cooling means for cooling uniform solutions within the reaction containers without cooling the above described reaction containers so that two-phase solutions are gained within the reaction containers, a syringe with a cooling apparatus, an apparatus for placing a solid having a temperature that is lower than the temperature of a reaction container into a uniform solution within the reaction container, and a mixing apparatus for mixing a low boiling point compound directly into a uniform solution within a reaction container can be cited.

As for the control means for controlling the time of the start of operation and the time of the stop of the operation in the respective operations: the sampling operation using the above described sampling means, the stirring operation using the stirring means, and the cooling operation using the cooling means, a well-known computer control, which follows the respective operation programs, can be cited as an example.

Next, the second invention is described. In a method for making a two-phase solution of which the phase state changes as a result of temperature conversion react according to the present invention, the reaction step is a step for making a material solution react by stirring the material solution within a reaction container at a predetermined temperature and thus gaining a uniform solution. The reaction solvent of the material solution is a solution where the state of phase, that is, the state of a two-phase solution and the state of a uniform solution, is changed in a reversible manner when the temperature fluctuates over and under a certain constant temperature (hereinafter also referred to as "solvent mixture"). Though this solvent mixture is not particularly limited, a solvent mixture of an organic solvent having a low polarity and an organic solvent having a high polarity can be cited as an example.

As for the organic solvent having a low polarity, alkane, cycloalkane, alkene, alkyne, aromatic compounds and the like can be cited as examples. From among these, cycloalkane compounds are preferable. As the cycloalkane compound, cyclohexane, methyl cyclohexane, decalin and the like can be cited as examples, and from among these, cyclohexane has a relatively high melting point of 6.5° C., and thus, is preferable in that the product of reaction, for example, can be solidified and separated.

As for the organic solvent having a high polarity, nitroalkane, nitrile, alcohol, alkyl halide, carbonate, imidazolidinone, carbodiimide, ester, carboxylic acid, aldehyde, ketone, ether, urea, amide compounds and sulfoxide can be cited as examples, and one type can be used alone, or two or more types can be combined for use.

The material solution that is used in the present invention contains a variety of substances which relate to the reaction, such as a solute, a catalyst, a ground substance and a reaction adjuvant, in addition to the solvent mixture. As concrete examples of the material solution, a mixed solution of cyclohexane, dimethyl formamide, octadecyl amine and benzoyl chloride, a mixed solution of cyclohexane, dimethyl formamide, octadecyl amine and acetic acid anhydride, a mixed solution of cyclohexane, N,N'-dimethyl imidazolidinone, octadecyl alcohol and benzoic acid, and a mixed solution of decalin, N,N'-dimethyl imidazolidinone, hexadecanethiol and methyl acrylate can be cited. In the above description, octadecyl amine, octadecyl alcohol and hexadecanethiol dissolve in cyclohexane or decalin, and the above described benzoyl chloride, acetic acid anhydride and methyl acrylate dissolve in dimethyl formamide, N,N'-dimethyl imidazolidinone, and the like.

The method for setting the material solution at a predetermined temperature within the reaction container is not particularly limited, and a method for introducing a material solution that has been heated to a predetermined temperature in advance into a reaction container, a method for introducing a material solution at room temperature into a reaction container, and after that, maintaining the material solution at a predetermined temperature by turning on the heater for heating the reaction heater, and a method for setting a reaction container to a temperature which exceeds a predetermined temperature by turning on the heater for heating the reaction container and introducing the material solution at room temperature into this reaction container so that the material solution is maintained at the predetermined temperature can be cited as examples. From among these, the method using the heater for heating the reaction container is preferable in that a separate container for heating the material solution is not required. The predetermined temperature is a reaction temperature that is appropriately determined on the basis of the type of material solution and reaction. In the reaction step, the method for stirring the sample that has been heated to a predetermined temperature is not particularly limited, and a mechanical stirring method for stirring with a stirring rod with stirring blades on the end portion, a bubbling method for introducing bubbles by blowing a nitrogen gas into a sample, and a vibration stirring method for making a sample container or a sample vibrate can be cited as examples. From among these, the mechanical stirring method for stirring with a stirring rod with stirring blades on the end portion or the bubbling method for introducing bubbles by blowing a nitrogen gas into a sample are preferable, in that the required apparatus is simple and the efficiency in stirring is high. The solvent mixture that is used in the present invention does not become a uniform solution simply by being heated to a predetermined temperature, but rather, the phases dissolve each other by providing constant physical stimulation. Accordingly, appropriate stirring conditions for the reaction step are selected as conditions for gaining a uniform solution. After a uniform solution has been gained, it may be maintained for a predetermined period of time at the predetermined temperature. The predetermined period of time is the time for reaction, and an appropriate period is determined on the basis of the type of the solvent used, the reaction and the purpose of the reaction. Phase separation naturally occurs in the solvent mixture that is used in the present invention when the temperature lowers, and therefore, a uniform solution is maintained at a temperature that is no lower than the temperature at which phase separation occurs during the predetermined period of time.

The cooling step is a step for gaining a two-phase solution within the reaction container by cooling the uniform solution without cooling the reaction container. As the method for cooling the uniform solution without cooling the reaction container, though there is no special limitation, a method for extracting a portion or the entirety of the uniform solution from the reaction container, cooling the extracted uniform solution with a cooler, and returning the two-phase solution gained through this cooling to the reaction container, a method for putting a solid of which the temperature is lower than that of the reaction container in the uniform solution within the reaction container, and a method for directly mixing a compound having a low boiling point into the uniform solution within the reaction container can be cited. "Without cooling the reaction container" means the opposite of cooling the sample within the reaction container by cooling the reaction container, and includes cooling of the reaction container when the sample within the reaction container is cooled.

According to the method for extracting a portion or the entirety of the uniform solution from the reaction container, cooling the extracted uniform solution with a cooler, and returning the two-phase solution gained through this cooling to the reaction container, as the apparatus that is used in this method, a sampler with a cooling apparatus, for example, can be used in the case where the apparatus is a small-scale reaction apparatus. This sampler has the same mechanism as a syringe, and as the cooling apparatus, an apparatus where water is made to flow through a jacket that is formed around the cylinder of the sampler, for example, can be used. In addition, in the case of a large-scale reaction apparatus, an external cooling unit apparatus which is formed of an external cooler, a pump and pipes for linking these to form a circulation system can be used.

In addition, in accordance with the method for putting a solid of which the temperature is lower than that of the reaction container in the uniform solution within the reaction container, as the apparatus that is used in the method, a glass rod or a metal rod with a cooling apparatus can be cited as an example. In addition, as the compound having a low boiling point that is mixed into the uniform solution within the reaction container, n-heptane, of which the boiling point is 25° C., can be cited as an example. When a low boiling point compound makes direct contact with the uniform solution within the reaction container, it absorbs evaporation heat from the solution, thus cooling the solution. The evaporated compound having a low boiling point is liquefied by a gas vaporizer, and is put back in the reaction container. The uniform solution can be cooled by repeating this procedure. The uniform solution that has been cooled in accordance with the above described method automatically separates into two phases when the temperature is no higher than a predetermined temperature. In the two-phase solution that is gained in the cooling step, one phase is made of a product solution where a product of reaction has been dissolved in an organic solvent having a low polarity, such as cyclohexane, and the other phase is made of a solution where a catalyst or a reaction adjuvant has been dissolved in an organic solvent having a high polarity, such as dimethyl formamide.

In the cooling step, a two-phase solution is gained within the reaction container after cooling. In the case where the cooling method is a method using a solid of a low temperature or a method using a compound having a low boiling point, phases are separated within the reaction container, and therefore, no specific operation is required, and the solution can be left as it is. Meanwhile, in the case of the method for extracting a portion or the entirety of the uniform solution from the reaction container and cooling the extracted uniform solution with a cooler, the two-phase solution that was gained through cooling is returned to the inside of the reaction container. As the cooling method in the cooling step, the method for extracting a portion or the entirety of the uniform solution from the reaction container and cooling the extracted uniform solution with a cooler is preferable. That is to say, in the case of cooling within the reaction container using a solid of a low temperature or a compound having a low boiling point, the reaction container being heated is also cooled, making the efficiency in cooling poor. Furthermore, since the reaction container cools down, it becomes necessary to heat the remaining solvent at the time of reuse after the product solution is extracted, and thus, the cost of the reaction increases. In contrast, according to the method for cooling with an external cooling apparatus or cooler, it is possible to cool only the reaction solution, thus making the efficiency in cooling high. In addition, even when the solution that has been separated into two phases is heated after being put back into the reaction container being heated, there is no physical stimulation, and therefore, the state where the solution is separated into two phases can be maintained.

After the cooling step, the phase of the product solution is extracted from the two-phase solution that was gained within the reaction container, and is used for the intended application as it is, or after the solvent has been removed, if necessary. In addition, in the case where a multi-stage consecutive reaction process is carried out, it is preferable to leave the solvent phase that has been left after the extraction of the phase of the product solution to be left as it is within the reaction container being heated, in order to minimize the thermal energy for heating the reaction container again at the time of reuse of the remaining solvent phase, and thus suppress the cost for reaction.

In addition, the reaction apparatus used for the two-phase solution of which the phase state changes when as a result of temperature conversion according to the present invention is provided with a heating means for heating a reaction container, a reaction container with a stimulating means for physically stimulating a material solution within the reaction container so as to gain a uniform solution, and a cooling means for cooling the uniform solution within the reaction container without cooling the reaction container.

As for the heating means for heating the reaction container, though there are no particular limitations, an embedded heater that is provided within a wall of the reaction container can be cited as an example. This heater is connected to a temperature control mechanism for usually controlling the temperature within the reaction container.

As for the stimulating means for physically stimulating the material solution within the reaction container so as to gain a uniform solution, a stirring rod with stirring blades on the end portion, a bubbling apparatus with a bubble introducing pipe for introducing bubbles into the material solution and a bubble generator, and a vibrator for making the reaction container or the material solution vibrate can be cited as examples.

As for the cooling means for cooling the uniform solution within the reaction container without cooling the above described reaction container, a means for extracting the uniform solution from the reaction container, cooling the extracted uniform solution with a cooler, and returning the two-phase solution that was gained through cooling into the reaction container, a means for putting a solid of which the temperature is lower than the temperature of the reaction container in the uniform solution within the reaction container, and a mixing means for mixing a compound having a low boiling point directly into the uniform solution within the reaction container can be cited.

Next, the first invention is described further concretely by citing an example, but this is merely illustrative, and does not limit the present invention.

EXAMPLE 1

A tabletop apparatus having a built-in block heater containing 100 cylindrical glass receptacles having a diameter of 20 mm and a height of 60 mm as reaction containers was used, and chemical reactions were made to occur through a great number of processes automated by a computer, following the method shown in FIG. 2(A) and under the below described conditions for reaction.
(Samples and Temperature of Reaction Containers)

100 samples where octadecyl amine and benzoyl chloride were mixed with a variety of ratios into a solvent mixture made of 2 ml of cyclohexane and 2 ml of dimethyl formamide (DMF) were prepared. In addition, the block heater was turned on and the reaction container was heated in advance so that the temperature became 60° C. Here, in the following steps, the temperature was adjusted so that the temperature of the reaction containers always became 60° C.
(Sample Heating Step)

The 100 samples that were prepared were sequentially put into the first to one hundredth reaction containers, which had been heated to 60° C. After the samples were put into the 100 reaction containers, the procedure was taken to the next step, at the point in time when the two-phase solution in the reaction containers became 50° C.
(Reaction Step)

The two-phase solution in the 100 reaction containers that were heated to 50° C. was sequentially stirred with a stirring rod, so that respective uniform solutions were gained, and left for a predetermined period of time so as to make reaction occur. The two-phase solutions became uniform solutions immediately after stirring. The period of time ($t_B$) from the start of the putting of the solution into the 100 reaction containers to the start of physical stirring with a stirring rod was 120 minutes.
(Cooling Step)

Next, a syringe with a cooling apparatus was used, and 3.8 ml of uniform solution was drawn into this syringe from the first reaction container and left undisturbed within the syringe, and then, the solution was separated into two phases when the temperature of the solution lowered to approximately 40° C. After the solution was left for an additional two minutes, the solution was gradually returned from the syringe to the first reaction container which was heated to 60° C. When this solution was left, the temperature returned to no lower than 48° C., but the two-phase state was maintained, because no physical stirring was carried out. This operation was carried out on the second to one hundredth samples. The period of time ($t_C$) from the start of the physical stirring to the start of cooling was 120 minutes for all of the samples.

In the above described example, chemical processes can be carried out on a large number of samples under the same conditions through the automatic operation of one multiple process automatic chemical reaction apparatus. In addition, this apparatus, including accessory apparatuses, is a simple apparatus and is excellent in operability and reproducibility. In addition, in the cooling step, the product solution in the two-phase solution that was gained in a heated reaction container was extracted for chemical analysis using a syringe, while the remaining solvent in a heated state can be reused as it is. Therefore, reheating is unnecessary, and thus, the cost for reaction can be reduced.

Next, the second invention is described further concretely by citing examples, but these are merely illustrative, and do not limit the present invention.

EXAMPLE 2

A tabletop apparatus having a built-in block heater having cylindrical glass receptacles having a diameter of 20 mm and a height of 60 mm as reaction containers was used, and chemical reactions were made to occur through processes under the following reaction conditions. 2 ml of cyclohexane in which octadecyl amine (51 milligrams) was dissolved, and 2 ml of dimethyl formamide (DMF) in which benzoyl chloride (49 milligrams) was dissolved were put into a reaction container of which the temperature was 25° C. so as to prepare a material solution. At this time, the liquid separated into two phases.

Next, the reaction container was heated so that the temperature became 60° C., and at the point where temperature of the solution reached 48° C., a nitrogen gas was blown directly into the solution and physical stirring was carried out, so that the solution immediately became a uniform solution. Next, a cooler in syringe form with a cooling apparatus was used, and 3.6 ml of the uniform solution was drawn into the cooling container from the main process container and left undisturbed, and then, the solution separated into two phases when the temperature fell to approximately 40° C. After the solution was left for an additional two minutes, the liquid was gradually returned from the cooler to the main process reaction container that was heated to 60° C. Though this solution returned to no lower than 48° C. when left as it is, no strong physical stirring, such as blowing in of a nitrogen gas, was carried out, and the state of two phases was maintained.

The product solution portion which was the upper phase in the two-phase solution within the reaction container in the heated state of 60° C. was extracted, and the solvent was removed, and it was confirmed that the product of reaction was N-octadecylbenzamide (yield: 96%). In addition, the solution that remained within the reaction container was a dimethyl formamide solution which was heated to no lower than 48° C. and in which benzoyl chloride was dissolved, and was in such a state as to be reusable as a portion of a material solution for the reaction in the next stage.

EXAMPLE 3

A tabletop apparatus having a built-in block heater having cylindrical glass receptacles having a diameter of 20 mm and a height of 60 mm as reaction containers was used, and chemical reactions were made to occur through processes under the following conditions for reaction. 2 ml of cyclohexane in which 2-amino butyric acid 3,4,5-tris octadecyloxy benzyl ester (60 milligrams) was dissolved, and 2 ml of dimethyl formamide (DMF) in which 9-fluorenyl methoxy carbonyl amino acetic acid (57 milligrams), diisopropyl carbodiimide (25 milligrams) and 1-hydroxy benzotriazole (55 milligrams) were dissolved, and which was stirred for 90 minutes, were put in a reaction container of which the temperature was 25° C., so that a material solution was prepared. At this time, the liquid separated into two phases.

Next, the reaction container was heated so that the temperature became 60° C., physical stirring was carried out with a stirring rod with stirring blades at the end at the point where the temperature of the solution reached 48° C., and then, the solution immediately became a uniform solution. Next, a glass rod having a diameter of 8 mm with a cooling apparatus which was cooled to 5° C. was put in the main process solution so as to lower the temperature of the solution, and thereby, the solution separated into two phases. After the solution separated into two phases, the glass rod with the cooling apparatus was pulled out, and the solution was left as it is. The temperature of the solution increased afterwards, and even when the temperature became no less than 48° C., the state where the solution was separated into two phases was maintained.

When the product solution portion which was the upper phase in the two-phase solution within the reaction container in a heated state of 60° C. was extracted, and the solvent was removed, 2-[2-(9H-fluoro-9-ylmethoxy carbonyl-amino)-acetyl amino]-3-methyl-butyric acid 3,4,5-tris octadecyloxy benzyl ester, which was the target product of reaction, was gained with a yield of 95%.

EXAMPLE 4

A tabletop apparatus having a built-in block heater having cylindrical glass receptacles having a diameter of 20 mm and a height of 60 mm as reaction containers was used, and chemical reactions were made to occur through processes under the following conditions for reaction. 2 ml of cyclohexane in which octadecyl amine (51 mg) was dissolved, and 2 ml of dimethyl imidazolidinone (DMI) in which acetic acid anhydride (20 mg) was dissolved was put into a reaction container of which the temperature was 25° C., so that a material solution was prepared. At this time, the liquid separated into two phases.

Next, the reaction container was heated so that the temperature became 60° C., and at the point where the temperature of the solution reached 48° C., a nitrogen gas was blown directly into the solution, and physical stirring was carried out, and then, the solution immediately became a uniform solution. Next, n-pentane of which the temperature was 25° C. was gradually poured into this uniform solution. The N-pentane immediately started vaporizing, and at the point where the solution separated into two phases, the n-pentane stopped being poured. The n-pentane almost completely vaporized when left for approximately 10 minutes, and even when the temperature of the solution became no lower than 48° C., the state where the solution was separated into two phases was maintained.

When the product solution portion which was the upper phase in the two-phase solution within the reaction container in a heated state of 60° C. was extracted, and the solvent was removed, N-octadecyl acetamide was gained (yield: 97%).

INDUSTRIAL APPLICABILITY

A multiple process reaction method for a two-phase solution of which the phase state changes as a result of temperature conversion and a reaction apparatus for implementing this according to the first invention can be used effectively in high throughput liquid handlers, liquid phase multi-process apparatuses and liquid phase combinatorial synthesizing apparatuses. Accordingly, these are used by makers of combinatorial synthesizing apparatuses, in the pharmaceutical industry, by makers of analyzing and synthesizing apparatuses, makers of diagnosis apparatuses, makers of reagents for testing and research and the like. In addition, a method for making a two-phase solution of which the phase state changes as a result of temperature conversion react and an apparatus that is used for this according to the second invention can be applied to tabletop chemical process apparatuses for testing and research, flow system chemical reaction apparatuses and large-scale reaction plants.

The invention claimed is:

1. A method, comprising:
heating a material solution comprising a reactant and a two-phase reaction solvent comprising a first phase comprising a nonpolar solvent and a second phase comprising a polar solvent to a reaction temperature in a reaction container;
stirring the material solution, such that the first phase and the second phase of the two-phase reaction solvent dissolve each other to form a one-phase solution;
maintaining the one-phase solution, with stirring, at the reaction temperature for a predetermined period of time, to obtain a one-phase product solution comprising a reaction product;
drawing the one-phase product solution within the reaction container into an extraction apparatus and cooling the one-phase product solution outside the reaction container to a predetermined temperature below the reaction temperature without cooling the reaction container, to obtain a two-phase product solution comprising a solvent phase comprising the polar solvent and a product phase comprising the reaction product and the nonpolar solvent; and then,
returning the two-phase product solution, without stirring, to the reaction container, wherein the two-phase product solution is maintained.

2. The method of claim 1, further comprising, after the cooling:
extracting the product phase from the two-phase product solution.

3. The method of claim 2, wherein the solvent phase remains in the reaction container after extracting the product phase and is employed as the second phase of the two-phase reaction solvent in a subsequent reaction.

4. The method of claim 1, wherein the first phase of the two-phase reaction solvent comprises a cycloalkane compound, and wherein the second phase of the two-phase reaction solvent comprises at least one selected from a nitroalkane, a nitrile, an alcohol, an alkyl halide, a carbonate, an imidazolidinone, a carbodiimide, an ester, a carboxylic acid, an aldehyde, a ketone, an ether, a urea, an amide, and a sulfoxide.

5. The method of claim 1, wherein the first phase of the two-phase reaction solvent is an alkane, a cycloalkane, an alkene, an alkyne, or an aromatic compound.

6. The method of claim 5, wherein the first phase of the two-phase reaction solvent is a cycloalkane compound.

7. The method of claim 6, wherein the cycloalkane compound is cyclohexane.

8. The method of claim 6, wherein the cycloalkane compound is methyl cyclohexane.

9. The method of claim 6, wherein the cycloalkane compound is decalin.

10. The method of claim 1, wherein the second phase of the two-phase reaction solvent is a nitroalkane, a nitrile, an alcohol, an alkyl halide, a carbonate, an imidazolidinone, a carbodiimide, an ester, a carboxylic acid, an aldehyde, a ketone, an ether, a urea, an amide compound, or a sulfoxide.

11. The method of claim 10, wherein the second phase of the two-phase reaction solvent is an amide compound.

12. The method of claim 11, wherein the amide compound is dimethyl formamide.

13. The method of claim 10, wherein the organic solvent having a high polarity is an imidazolidinone compound.

14. The method of claim 13, wherein the imidazolidinone compound is dimethyl imidazolidinone.

15. The method of claim 6, wherein the second phase of the two-phase reaction solvent is an amide compound.

16. The method of claim 6, wherein the second phase of the two-phase reaction solvent is an imidazolidinone compound.

* * * * *